United States Patent [19]

Woods

[11] Patent Number: 4,694,679

[45] Date of Patent: Sep. 22, 1987

[54] GRAVITOMETER PROVER

[75] Inventor: James A. Woods, Houston, Tex.

[73] Assignee: Harold R. Lauterbach, Houston, Tex.

[21] Appl. No.: 847,440

[22] Filed: Apr. 2, 1986

Related U.S. Application Data

[63] Continuation-in-part of Ser. No. 636,836, Aug. 10, 1984, abandoned.

[51] Int. Cl.$^4$ ............................................. G01N 9/04
[52] U.S. Cl. ...................................................... 73/1 R
[58] Field of Search ................. 73/1 R, 433, 434, 435, 73/436, 437

[56] References Cited

U.S. PATENT DOCUMENTS 3,298,221 1/1967 Miller et al. ........................ 73/32 A
4,570,476 2/1986 Davis ..................................... 73/1 R

OTHER PUBLICATIONS

2 Page Brochure Entitled "Arcco-Anubis Gravitometer Prover", by Arcco Instrument Co., Inc., of 7144 E. Condor St., Los Angeles, Ca 90040; Published by Jul. 1984.

Primary Examiner—Tom Noland
Attorney, Agent, or Firm—Glaser, Griggs & Schwartz

[57] ABSTRACT

A gravitometer prover for measuring the density of a fluid for proving the accuracy of a gravitometer including an inner chamber member formed having an inner chamber for receiving fluid therein and an outer shell mounted about the inner chamber member in sealable relation thereto forming a cavity between the outer surface of the inner chamber member and the inner surface of the outer shell and a vacuum source in communication with the cavity for selectively imposing a vacuum in the cavity. A siphon tube removes solid particles entrained in test fluid as the inner chamber is charged. An orifice aperture vents gas components from the inner chamber.

4 Claims, 4 Drawing Figures

GRAVITOMETER PROVER

CROSS REFERENCE TO RELATED APPLICATION

This application is a continuation-in-part of U.S. application Ser. No. 636,836 filed Aug. 10, 1984 now abandoned.

FIELD OF THE INVENTION

The present invention relates generally to gravitometers and in particular to prover instruments which are used to verify the accuracy of gravitometers.

DESCRIPTION OF THE PRIOR ART

Gravitometers have long been used for determining the density of fluids, particularly when such fluids comprehend compressible, volatile liquids at high pressures. Various types of devices have been used in combination with gravitometers for determining the specific gravity of fluid within a flow line such as that shown in U.S. Pat. No. 3,477,277. While insulating jackets have been used in the past with devices such as a densitometer as shown in U.S. Pat. No. 3,298,221, such similar types of jacketed vessels have been in use for substantial periods of time as shown in U.S. Pat. No. 283,165. U.S. Pat. No. 2,179,892 discloses a vacuum vessel for use with a gravity determining apparatus while U.S. Pat. No. 4,374,474 discloses a pressurized density measuring device utilizing weighing principles for the determination of fluid density in a pressurized state.

While such density measuring devices have been known in the prior art, gravitometer provers have also been known which are used for determining the accuracy of a liquid gravitometer by weighing, such as those manufactured by Arcco Instrument Company, Inc. of Los Angeles, Calif. However, such provers typically utilize a specific volume of an exact size which is thereafter filled and weighed in order to determine the accuracy of readings of the gravitometer. Any damage to the chamber container, hence volume, can result in prover errors. Furthermore, particularly when such provers are used in determining the accuracy of a gravitometer used for measuring compressible, volatile liquids at high pressure, in an environment subject to high humidity, it is not unusual for sweating or condensation to occur about the exterior of the gravitometer prover. Such sweating or condensation results in additional weight being added to the prover, which may affect the accuracy of the prover tests.

The accuracy of the prover instrument can be further affected by the accumulation of heavy liquids or solid particles in the lower region of the prover chamber, and also by the accumulation of entrained gas bubbles in the upper portion of the sphere during flowing conditions. Preferably, the instrument is filled with a fluid having uniform density. The presence of trapped gas prevents the prover chamber from being completely filled, and the presence of solid particles and heavy fluids results in additional weight being added to the prover, all of which impairs the accuracy of the prover test.

So far as is known, there is no gravitometer currently available which is capable of insuring the protectability of the volume of a measuring chamber while also eliminating errors induced by the accumulation of condensate, solid particles or trapped gas.

SUMMARY OF THE INVENTION

The present invention relates to a new and improved gravitometer prover for measuring the density of a fluid in communication with and for proving the accuracy of a gravitometer including an inner shell formed having an inner chamber for receiving fluid therein and an outer shell mounted about the inner shell in a sealable relation thereto for forming a cavity between the outer surface of the inner shell and the inner surface of the outer shell for selectively permitting the imposition of a vacuum in the cavity for avoiding environmentally imposed errors and further to protect the inner chamber member from damage. A siphon tube removes solid particles entrained in test fluid as the inner chamber is charged. An orifice aperture vents gas components from the inner chamber.

DESCRIPTION OF THE PREFERRED EMBODIMENT

Figure 1:
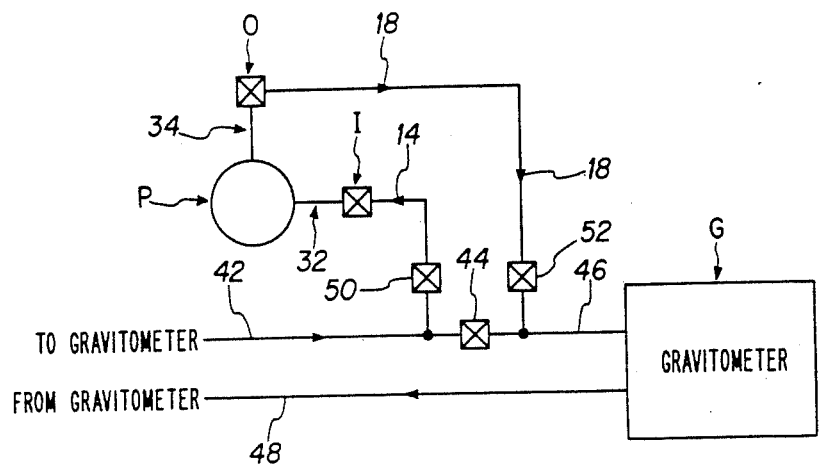
FIG. 1 is a schematic flow diagram detailing use of the gravitometer prover of the present invention as used with a gravitometer.

As shown in the drawings, the gravitometer prover of the present invention is designated generally with the letter P. The gravitometer prover P is adapted to be used with and for proving the accuracy of a gravitometer G. Generally speaking, the gravitometer prover P includes an inner chamber member C, a fluid inlet I, a fluid outlet O, an outer shell S and vacuum means V. Unless otherwise specified, it is preferred that the components of the gravitometer prover P of the present invention be made of stainless steel or some other high strength materials capable of withstanding the extremes in temperatures and pressures routinely encountered in the use of such gravitometer provers.

Figure 2:
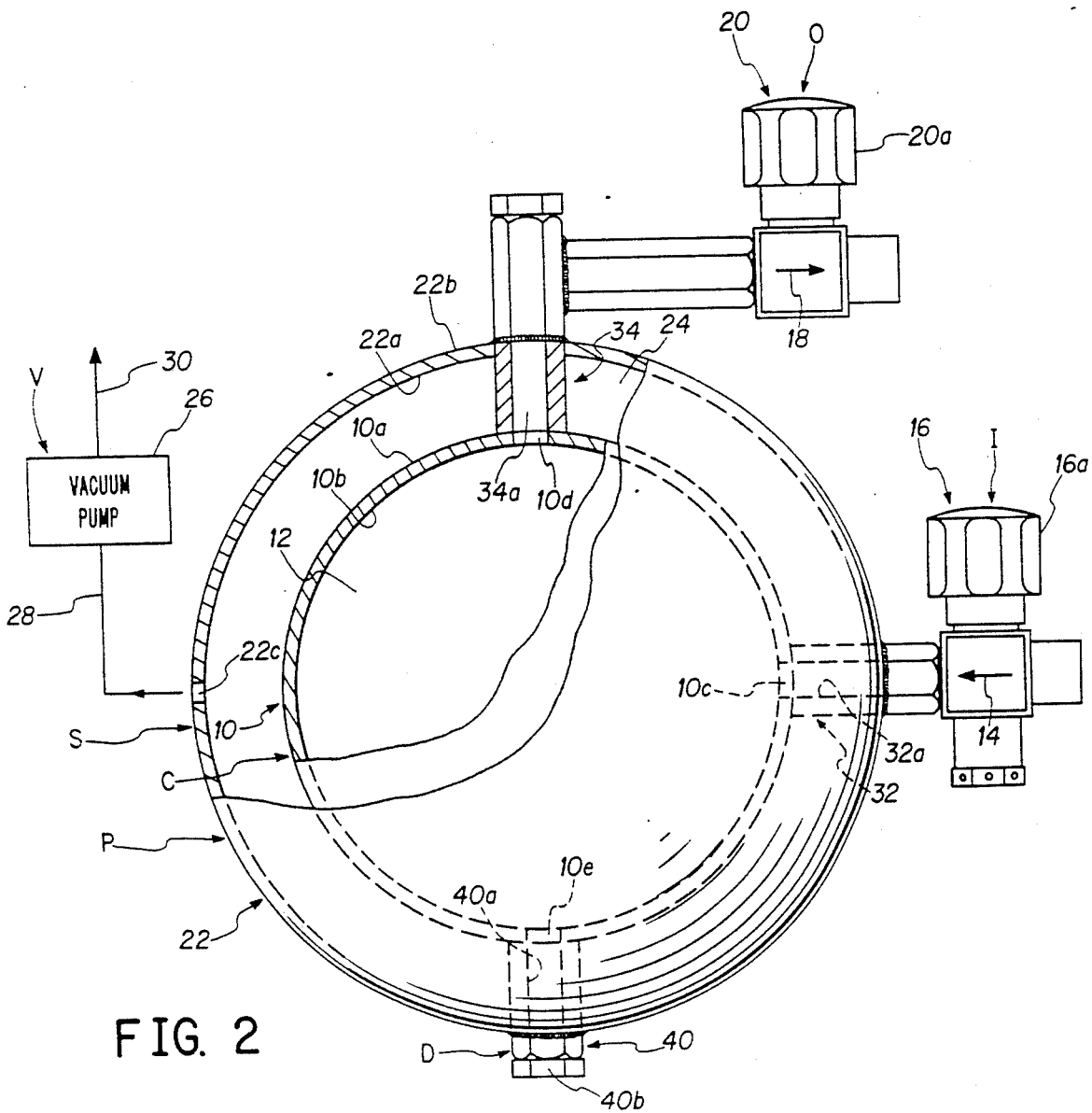
FIG. 2 is an elevational view, partly in section, of the gravitometer prover of the present invention.

As best seen in FIG. 2, the gravitometer prover P of the present invention includes an inner chamber member C. The inner chamber member C includes member 10 formed having an outer surface 10a, and an inner surface 10b. The inner surface 10b defines an inner chamber 12. Preferably the inner chamber member is of a spherical configuration; however, any other suitable configuration may be used.

The gravitometer prover P further includes a fluid inlet I in communication with the inner chamber 12 for receiving fluid flowing in the direction of arrow 14 to be directed into the chamber 12. The fluid inlet I further includes inlet valve means 16 for selectively regulating the communication of the fluid with the inner chamber 12. The inlet valve means 16 may include a valve 16a of any suitable type and variety capable of opening, closing and selectively regulating the flow of fluid through the fluid inlet I.

In similar fashion, the gravitometer prover P further includes fluid outlet O in communication with the inner chamber 12 for directing fluid from the inner chamber 12 in the direction of arrow 18. The fluid outlet O includes outlet valve means 20 with the fluid outlet O for selectively regulating communication of the fluid from the inner chamber 12. The outlet valve means 20 may include any suitable valve 20a capable of regulating, opening or closing fluid flow from the inner chamber 12 outwardly therefrom.

The gravitometer prover P of the present invention further includes an outer shell S mounted about the inner chamber member C in spaced relation thereto. The outer shell S includes shell 22 having an inner surface 22a and an outer surface 22b. As with the inner chamber member C, the outer shell S is preferably of a spherical configuration; however, any other suitable configuration is satisfactory. A cavity 24 is formed between the outer surface 10a of the inner chamber member C and the inner surface 22a of the outer shell S.

The gravitometer prover P of the present invention further includes vacuum means V in communication with the cavity 24 for selectively imposing a vacuum in the cavity 24. The vacuum means V includes a suitable vacuum pump 26 in communication with the cavity 24 by means of flow line 28 which is connected with cavity 24 by means of opening 22c formed in the outer shell 22.

Exhaust from the vacuum pump 26 is directed outward therefrom through flow line 30. When desired, a suitable vacuum may be imposed in the cavity 24 by the vacuum means V, and the vacuum may thereafter be retained in the cavity 24 by removal of the flow line 28 and plugging the opening 22c with a suitable plug (not shown) in a known fashion.

The gravitometer prover P further includes an inlet conduit 32 disposed in the cavity 24 between the outer surface 10a of the inner chamber member C and the inner surface 22a of the outer shell 22 with the inlet conduit 32 being in communication with the fluid inlet I and the inner chamber 12. The inner conduit 32 typically includes a suitable passageway 32a for receiving fluid flowing into the inner chamber 12 which is directed from passageway 32a through opening 10c formed in member 10 thereinto inner chamber 12.

In similar fashion, an outlet conduit 34 is disposed in the cavity 24 between the outer surface 10a of the member 10 and the inner surface 22a of the outer shell 22. The outlet conduit 34 preferably communicates with the fluid outlet O and the inner chamber 12. The outlet conduit 34 further includes a passageway 34a formed therein for permitting such communication between the inner chamber 12 and the fluid outlet O, with the passageway 34a being aligned with opening 10d formed in the member 10.

The gravitometer prover P of the present invention further includes a drain member D disposed in the cavity 24 between the outer surface 10a of the member 10 and the outer shell S for permitting selectable draining of the inner chamber 12 as desired. Preferably, the drain member D includes member 40 formed having a passageway 40a therein allowing fluid flow from the inner chamber 12 through opening 10e formed in inner chamber member C through passageway 40a and outwardly from the drain member D upon removal of the drain closure 40b from the member 40.

As best seen in FIG. 1, the gravitometer prover P of the present invention is adapted to be used for determining the accuracy of a gravitometer G. Typical gravitometer operations include fluid flow through flow line 42, through valve 44, through flow line 46 into the gravitometer G for gravitometer operation as is well known. Thereafter, the discharge fluids flow from the gravitometer G in flow line 48. In such typical gravitometer G operations, the valves 50, 52 are normally in a closed position.

Should it be desired that the gravitometer G be checked to verify the accuracy of readings thereby, the gravitometer prover P must be first weighed to determine its tare weight. Thereafter, the gravitometer prover P is connected to the flow network as shown in FIG. 1 and the valve 44 is closed and valves 50, 52 are opened along with the fluid inlet I and fluid outlet O to permit fluid flow through the gravitometer prover.

It will be appreciated that prior to initiating the fluid flow through the gravitometer prover P, it is necessary that a vacuum be imposed within the cavity 24 by selective action of the vacuum means V which includes operation of the vacuum pump 26 to draw a vacuum in the cavity 24 and thereafter plugging the opening 22c. The fluid flow through the gravitometer prover is maintained for a suitable period of time to ensure that the temperature and pressure within the gravitometer prover P are stablized. Thereafter, the inlet valve means 16 and outlet valve means 20 are closed as are valves 50 and 52.

The gravitometer prover with valves 16, 20 are removed from flow lines 14, 18 at the same time that the density indicated by the gravitometer G is noted. The interior volume of the inner chamber 12 is known very precisely, which by way of example, may typically be 1,000 cc±0.05 cc at 0 psia, 0° F. The gravitometer prover P is then weighed, with the tare weight being subtracted from the total weight to reveal the weight of the fluid contents.

The weight of the fluid contents is divided by the known volume to give the density of the contained fluid within the gravitometer prover P. The comparison of the determined density to the indicated reading on the gravitometer G proves the veracity of the gravitometer G readings. Typically a balance beam device is used to weigh the gravitometer prover P and as such, it is not unusual to be able to determine weights to the nearest 0.05 grams.

Furthermore, it is known that the volume-temperature correction factors are typically linear. Such provers P are certified for usage to 150° F. Using such parameters for typical values, the determined density using the gravitometer prover P of the present invention will be within ±0.0002 of the actual density, if the volume measurements are ±0.05 cc of the volume and the weight measurements are ±0.05 gram of weight of the measured fluid.

It should be appreciated that "fluid" has been used throughout this application in its broadest sense and as such, fluid includes gases or liquids for which gravimetric readings are desired.

Figure 3:
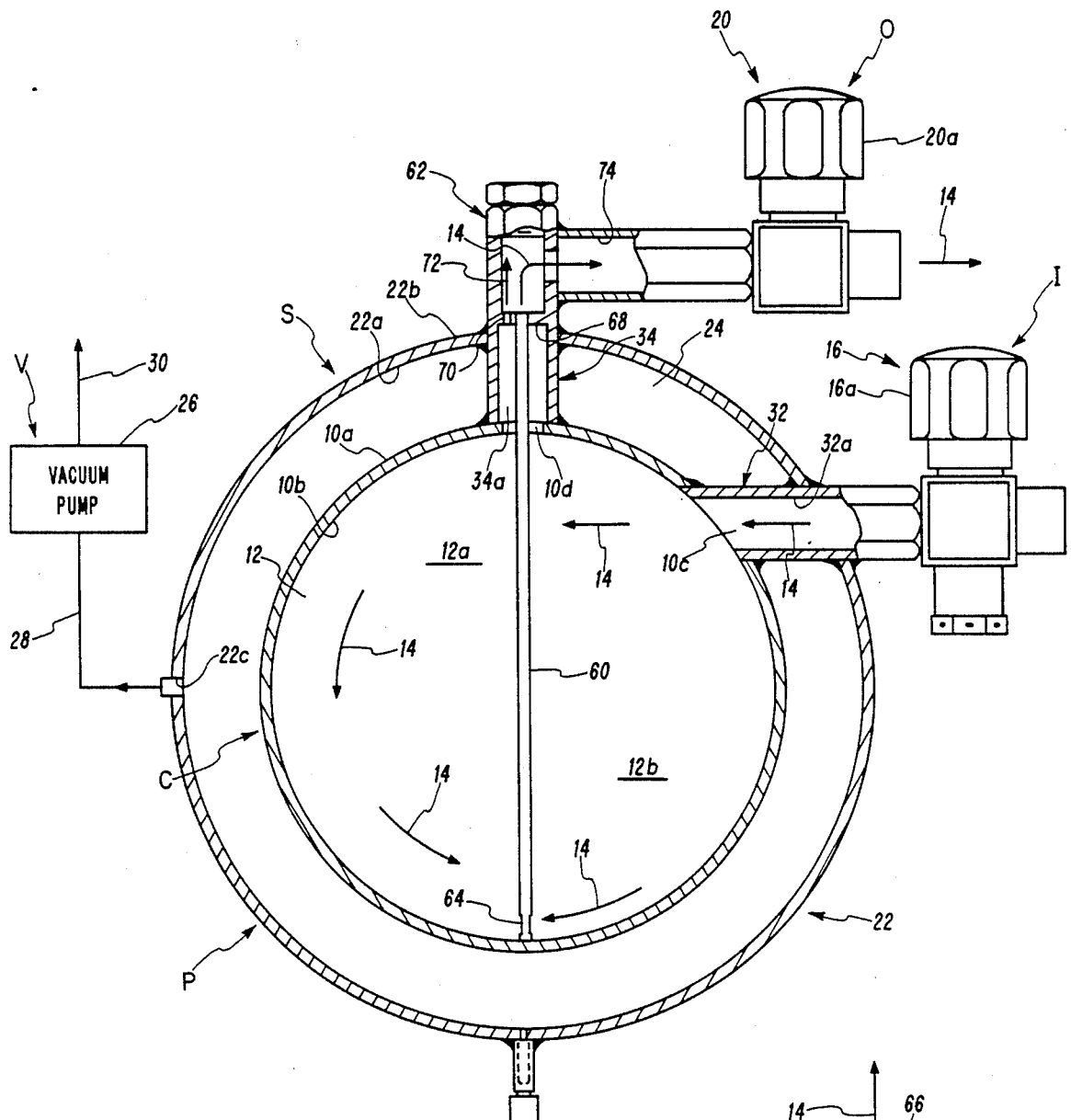
FIG. 3 is an elevational view, partly in section, of an alternative prover instrument constructed according to the teachings of the present invention; and, FIG. 4 is an enlarged view of a portion of the siphon tube assembly shown in FIG. 3.
Figure 4:
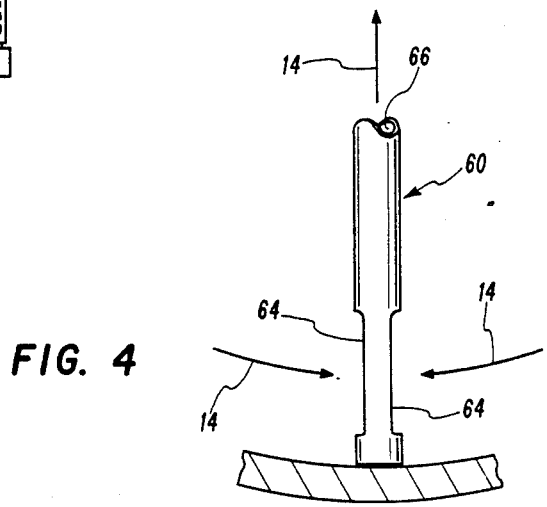

When the fluid under test is liquid, the accuracy of gravimetric readings can be influenced substantially by the presence of solid particulate material or gaseous components entrained within the test liquid. Preferably, the consistency of the test liquid is uniform, free of such entrained solids, and with no pockets of trapped gas occurring within the inner chamber 12. The foregoing test fluid conditions are accomodated by an alternative embodiment as illustrated in FIGS. 3 and 4. In this embodiment, the test fluid 14 is constrained to flow into an upper region 12A of the inner chamber member C and is withdrawn out of the chamber through an elongated siphon tube 60. In this arrangement, the flowing test liquid 14 enters the chamber 12 in a direction perpendicular to and coplanar with the vertical center line through the inlet 32. As it flows into the upper chamber 12A, it strikes the siphon tube 60 and the opposite side of the sphere C, creating both a scrubbing and a mixing action. The siphon tube 60 is connected to the top sphere fitting 62 which provides communication to the outlet valve O. The siphon tube 60 is seated on the bottom of the sphere and has a slot 64 for receiving the full flow to enter the siphon tube. This flow pattern, from the bottom of the sphere C, assures that heavy liquids or solid particles do not accumulate in the lower region 12B, which would result in an erroneous test reading. That is, relatively dense particulate matter or relatively dense liquid will enter the slot opening 64 and will be entrained in the flow of test liquid 14 as it exits through the siphon passage 66.

In that arrangement, the elongated siphon tube 60 serves as a flow-restricting means which restricts and constrains the flow of test liquid in such a manner that relatively dense components entrained in the flow will be carried out of the measurement chamber.

In some instances a substantial amount of gas will be entrained within the test liquid flow and become trapped within the chamber. The volume of test liquid displaced by the gas can, in some instances, be significant, thereby substantially affecting the accuracy of the instrument. This condition is accomodated in the present invention by an orifice plate 68 lodged in the flow passage 34A. Orifice plate 68 includes a vent aperture 70 which releases gases 72 which might otherwise accumulate within the test chamber 12 during flowing conditions.

It will be seen that the flow passage 66 of siphon tube 60 is coupled in serial fluid flow relation with the fluid flow outlet 74.

Thus, the gravitometer prover P of the present invention provides a new and improved device capable of enhanced protection of the inner chamber member C for prevention of damage to the precisely measured volume of the inner chamber 12 while further avoiding environmental complications by having the outer surface 10a of the member 10 being exposed to the environment. Such environment complications as high humidity are avoided by virtue of the vacuum imposed in the cavity 24 of the gravitometer prover P of the present invention. Errors induced by entrained solids and gases are avoided by the siphon tube and vent arrangement.

The foregoing disclosure and description of the invention are illustrative and explanatory thereof, and various changes in the size, shape and materials, as well as in the details of the illustrated construction may be made without departing from the spirit of the invention.

What is claimed is:

1. A gravitometer prover for measuring the density of a fluid in communication with and for proving the accuracy of a gravitometer, comprising:

a shell member having an outer surface and an inner surface defining an inner chamber for receiving fluid therein;

a fluid inlet formed in said shell member in communication with said inner chamber for receiving fluid to be directed into said inner chamber;

a fluid outlet formed in said shell member in communication with said inner chamber for directing fluid from said inner chamber; and, flow restricting means interposed between said inner chamber and said fluid outlet, said flow restricting means comprising an elongated tube projecting into said inner chamber, said elongated tube having an inlet port in communication with said inner chamber for admitting fluid and having an outlet port connected in communication with said fluid outlet.

2. A gravitometer prover as defined in claim 1, wherein said inner chamber is characterized by an upper region and a lower region relative to the direction of gravity flow, said elongated tube projecting through said upper region with its inlet port disposed within said lower region.

3. A gravitometer prover as defined in claim 1, wherein said elongated tube is substantially coextensive with a diameter of said shell member, the inlet end portion of said elongated tube engaging the inner surface of said shell member, and said inlet port comprising a slot formed in the sidewall of said elongated tube.

4. A gravitometer prover as defined in claim 1, said flow restricting means comprising:

an orifice plate having a flow aperture substantially smaller than said fluid outlet; and, said elongated tube coupled in parallel fluid flow relation with said orifice plate aperture.

* * * * *